US010022090B2

(12) United States Patent
Whitman (10) Patent No.: US 10,022,090 B2
(45) Date of Patent: Jul. 17, 2018

(54) NERVE PROTECTING DISSECTION DEVICE (71) Applicant: Atlantic Health System, Inc., a NJ non-profit corporation, Morristown, NJ (US)

(72) Inventor: Eric D. Whitman, Mountain Lakes, NJ (US)

(73) Assignee: Atlantic Health System, Inc., Morristown, NJ (US)

( * ) Notice: Subject to any disclaimer, the term of this patent is extended or adjusted under 35 U.S.C. 154(b) by 235 days.

(21) Appl. No.: 14/057,358

(22) Filed: Oct. 18, 2013

(65) Prior Publication Data
US 2015/0112325 A1    Apr. 23, 2015

(51) Int. Cl.
    *A61B 18/12*    (2006.01)
    *A61B 5/00*    (2006.01)
    *A61B 18/00*    (2006.01)

(52) U.S. Cl.
CPC .......... *A61B 5/6877* (2013.01); *A61B 5/4041* (2013.01); *A61B 5/4893* (2013.01);
(Continued)

(58) Field of Classification Search
CPC .. A61B 2018/00434; A61B 2018/0044; A61B 2018/00446; A61B 2018/00595;
(Continued)

(56) References Cited

U.S. PATENT DOCUMENTS 5,284,153 A    2/1994    Raymond et al.
5,560,360 A  * 10/1996    Filler et al. ................... 600/408
(Continued)

FOREIGN PATENT DOCUMENTS

WO    WO 96/39932    12/1996
WO    WO 2006/042075 A2    4/2006
(Continued)

OTHER PUBLICATIONS

David W. Eisele, M.D.; Intraoperative Electrophysiological Monitoring of the Recurrent Laryngeal Nerve; From Laryngyscope 106: Apr. 1996.

*Primary Examiner* — Jaymi Della
*Assistant Examiner* — Eunhwa Kim
(74) *Attorney, Agent, or Firm* — The McHattie Law Firm; Jonathan A. Tyler (57) ABSTRACT

The present invention provides an energy based dissection device that automatically provides a nerve protection function. Specifically, the present invention operatively connects nerve monitoring technology and energy based dissection technology to provide a device that provides energy based dissection functionality that cannot operate, or operates differently, upon receipt of real time information from the nerve monitoring functionality that nerve damage may be imminent in the absence of such safety shutdown. The present invention also creates a real-time graphical display of the nerve, including size and location relative to the energy based dissection device to enable the operator to safely and accurately avoid damaging the nerve. Accordingly, the present invention provides a surgical device that removes human error and reaction time issues which prevent unintended dissection and concomitant nerve damage.

18 Claims, 6 Drawing Sheets

(52) U.S. Cl.
CPC ............... *A61B 2018/0044* (2013.01); *A61B 2018/00434* (2013.01); *A61B 2018/00446* (2013.01); *A61B 2018/00595* (2013.01); *A61B 2018/00601* (2013.01)

(58) Field of Classification Search
CPC .......... A61B 2018/00601; A61B 2018/00839; A61B 18/00; A61B 5/4041; A61B 5/6877; A61B 5/4893
See application file for complete search history.

(56) References Cited

U.S. PATENT DOCUMENTS

| | | | |
|---|---|---|---|
| 5,928,158 A | | 7/1999 | Aristedes |
| 6,259,945 B1 | | 7/2001 | Epstein et al. |
| 6,535,759 B1 | | 3/2003 | Epstein et al. |
| 7,006,863 B2 | | 2/2006 | Maddess et al. |
| 7,214,197 B2 | | 5/2007 | Prass |
| 7,618,380 B2 | | 11/2009 | Mallinger et al. |
| 7,634,315 B2 | | 12/2009 | Cholette |
| 7,717,932 B2 | | 5/2010 | McFarlin et al. |
| 7,972,284 B2 | | 7/2011 | Mallinger et al. |
| 7,991,463 B2 | | 8/2011 | Kelleher et al. |
| 8,050,769 B2 | | 11/2011 | Gharib et al. |
| 8,241,313 B2 | | 8/2012 | McFarlin et al. |
| 2002/0077627 A1* | 6/2002 | Johnson | ............. A61B 18/1477 606/41 |
| 2003/0195405 A1* | 10/2003 | Marino et al. | ................ 600/373 |
| 2004/0015205 A1* | 1/2004 | Whitehurst | ........ A61N 1/37205 607/48 |
| 2004/0267243 A1 | 12/2004 | Klotz et al. | |
| 2005/0004559 A1* | 1/2005 | Quick | ................... A61B 10/02 606/1 |
| 2007/0100334 A1 | 5/2007 | McFarlin et al. | |
| 2008/0077198 A1* | 3/2008 | Webb et al. | .................... 607/88 |
| 2008/0103416 A1 | 5/2008 | Mallinger et al. | |
| 2009/0054804 A1 | 2/2009 | Gharib et al. | |
| 2009/0054908 A1 | 2/2009 | Zand et al. | |
| 2009/0105604 A1 | 4/2009 | Bertagnoli et al. | |
| 2009/0105788 A1 | 4/2009 | Bartol et al. | |
| 2010/0063376 A1 | 3/2010 | Kartush | |
| 2010/0145178 A1 | 6/2010 | Kartush | |
| 2010/0145222 A1 | 6/2010 | Brunnett et al. | |
| 2010/0179410 A1 | 7/2010 | Prass | |
| 2010/0198099 A1 | 8/2010 | Murphy et al. | |
| 2011/0060243 A1* | 3/2011 | Hausman et al. | ............ 600/554 |
| 2011/0237974 A1 | 9/2011 | Bartol et al. | |
| 2011/0270120 A1* | 11/2011 | McFarlin | ................. A61N 1/36 600/554 |
| 2012/0123292 A1* | 5/2012 | Fagin | ................ A61B 5/04001 600/554 |

FOREIGN PATENT DOCUMENTS

| | | |
|---|---|---|
| WO | WO 2006/113394 A2 | 10/2006 |
| WO | WO 2008/124079 A1 | 10/2008 |
| WO | WO 2012/106593 A2 | 8/2012 |

* cited by examiner

NERVE PROTECTING DISSECTION DEVICE

FIELD OF THE INVENTION

The present invention provides an energy based dissection device that automatically provides a nerve protection function. Specifically, the present invention operatively connects nerve monitoring technology and energy based dissection technology to provide a device that provides energy based dissection functionality that cannot operate, or operates differently, upon receipt of real time information from the nerve monitoring functionality that nerve damage may be imminent in the absence of such safety shutdown. The present invention also creates a real-time graphical display of the nerve, including size and location relative to the energy based dissection device to enable the operator to safely and accurately avoid damaging the nerve. Accordingly, the present invention provides a surgical device that removes human error and reaction time issues which prevent unintended dissection and concomitant nerve damage.

BACKGROUND

Energy based dissection devices are known. For example, U.S. Pat. No. 8,241,313 discloses a surgical cutting instrument for use with a drive motor, and related system and method, is described. The surgical cutting instrument includes an elongated drive member, a cutting tip secured to the drive member, a non-conductive coupling body adapted for connection to a motor assembly, a housing maintaining the coupling body, a fluid coupling assembly and an electrical connector for connection to a stimulating energy source. The electrical connector is in electrical communication with the cutting tip via an electrical pathway.

In another example, Ethicon Endo-Surgery, Inc. discloses their HARMONIC ACE® shears, a sterile, single-patient-use device consisting of an ergonomic grip housing assembly and two hand-controlled power settings. The HARMONIC ACE® shears employ an adaptive tissue technology enabling the generator to actively monitor the instrument during use, allowing the system to respond intelligently to varying tissue conditions. Electrical energy is converted to mechanical energy.

Nerve monitoring devices are also known. For example, U.S. Pat. No. 7,991,463 discloses systems for determining structural integrity of a bone within the spine of a patient, the bone having a first aspect and a second aspect, wherein the second aspect separated from the first aspect by a width and located adjacent to a spinal nerve. A stimulator is configured to generate an electrical stimulus to be applied to the first aspect of the bone. A monitor is configured to electrically monitor a muscle myotome associated with the spinal nerve to detect if an onset neuro-muscular response occurs in response to the application of the electrical stimulus to the first aspect of the bone. An adjuster is configured to automatically increase the magnitude of the electrical stimulus to until the onset neuro-muscular response is detected. Lastly, a communicator is configured to communicate to a user via at least one of visual and audible means information representing the magnitude of the electrical stimulus which caused the onset neuro-muscular response.

In another example, U.S. Pat. No. 7,972,284 discloses a method of preventing nerve damage positional injury during surgery includes providing a nerve damage positional injury pressure monitoring system including a site sensor with a transducer in the form of a transducer element and a ring extending outward from the transducer element, and a monitor connected to the site sensor; adhering the ring of the site sensor to the patient so that the transducer element forms a protective barrier in front of the area of the patient prone to nerve damage positional injury during surgery; using the system to continuously monitor pressure on the protective barrier formed by the transducer element in front of the area of the patient prone to nerve damage positional injury during surgery with the site sensor and monitor; and causing an alarm to be actuated to alert medical personnel of a pressure condition when monitored pressure is greater than a predetermined threshold.

In another example, U.S. Pat. No. 7,214,197 discloses an intraoperative neurophysiological monitoring system includes an adaptive threshold detection circuit adapted for use in monitoring with a plurality of electrodes placed in muscles which are enervated by a selected nerve and muscles not enervated by the nerve. Nerve monitoring controller algorithms permit the rapid and reliable discrimination between non-repetitive electromyographic (EMG) events repetitive EMG events, thus allowing the surgeon to evaluate whether nerve fatigue is rendering the monitoring results less reliable and whether anesthesia is wearing off. The intraoperative monitoring system is designed as a "surgeon's monitor," and does not require a neurophysiologist or technician to be in attendance during surgery. The advanced features of the intraoperative monitoring system will greatly assist neurophysiological research toward the general advancement of the field intraoperative EMG monitoring through post-surgical analysis. The intraoperative monitoring system is preferably modular, in order to allow for differential system pricing and upgrading as well as to allow for advances in computer technology; modularity can also aid in execution of the design.

In another example, U.S. Pat. No. 7,006,863 discloses a method and an apparatus for simultaneously assessing the functional status of component parts of the nervous system by presenting sparse stimuli to one or more parts of the sensory nervous system. Sparse stimuli consist of temporal sequences of stimulus conditions presented against a baseline null stimulus condition, where the non-null stimulus condition, or conditions, are presented relatively infrequently. The low probability of encountering a stimulus differing from a baseline or null stimulus condition in sparse stimulus sequences insures that gain control mechanisms within the nervous system will increase the neural response magnitude and also bias the measured responses to those neurone populations having such gain controls. The consequently increased response amplitudes ensure more reliably recorded responses than are obtained with non-sparse stimuli.

In another example, U.S. Patent Application No. 2010/0145222 discloses a nerve monitoring system [that] facilitates monitoring an integrity of a nerve.

In another example, Medtronic discloses its NIM-Response® 3.0 nerve monitoring system, an innovative, intraoperative nerve integrity monitor enabling surgeons to identify and confirm motor nerve function and monitor major motor nerves by monitoring electromyographical (EMG) activity from multiple muscles during minimally invasive or traditional open surgeries and in response to a change in nerve function, providing visual and/or audible alerts. This system also implements artifact detection software for reducing noise and real-time continuous nerve monitoring with its APS™ Electrode.

There have also been attempts to combine the technology of dissection devices with nerve monitoring technology. For example, U.S. Pat. No. 8,050,769 discloses systems and methods for determining nerve proximity, nerve direction, and pathology relative to a surgical instrument based on an identified relationship between neuromuscular responses and the stimulation signal that caused the neuromuscular responses.

In another example, U.S. Pat. No. 5,928,158 discloses an improved surgical instrument which is used for cutting of tissue. The instrument includes a sensor which identifies nerves within the patient which are proximate to the cutting member of the instrument. The entire assembly is hand held and includes both a surgical cutter such as a scalpel blade, scissors, or laser scalpel, as well as the electronics to stimulate nerves within the patient. The electronics monitor is positioned near the tip of the instrument to warn the surgeon of a proximate nerve so that the nerves are not inadvertently severed. In one embodiment of this invention, the scissors are incapacitated when a nerve is sensed to prevent an accidental cutting of the nerve.

In another example, U.S. Patent Application No. 2010/0198099 discloses a signal processing module includes an input module electronically coupled to a sensing probe of a nerve integrity monitoring system. The probe senses electrical signals from a patient during operation of an electrosurgical unit. The input module receives an input signal from the probe. An EMG detection module is coupled to the input module and is adapted to detect conditions in the input signal. The conditions are classified as a function of a level of electromyographic activity. An output module, coupled to the EMG detection module, provides an indication of electromyographic activity in the input signal based on the detected conditions.

In another example, U.S. Patent Application No. 2014/0267243 discloses a surgical scalpel, scalpel instrument and/or scalpel system (collectively, scalpel), particularly designed for use in a transverse carpal ligament surgical procedure, that evaluates an incision path with respect to a nerve in the incision path, and is used to perform the incision if appropriate. The scalpel emits an evaluation signal through a potential incision path through tissue captured by the scalpel. The scalpel utilizes the emitted evaluation signal to determine the presence of a nerve in the incision path. The dissection and evaluation (surgical) instrument includes a blade that is retractable relative to a target tissue capture area thereof. Evaluation may include determining the presence of a nerve before incision and/or the evaluating whether the target tissue has been appropriately captured. A warning is provided when the evaluation determines that a nerve is in the incision path and/or when the captured target tissue is determined to be inappropriate. Alternatively, the surgical instrument may disable extension of the blade when the evaluation determines that a nerve is in the dissection path and/or when the captured target tissue is determined to be inappropriate.

Therefore, there remains an unmet need for the system and method of the invention of the present application that operatively connects nerve monitoring technology and energy based dissection technology to provide a device that provides energy based dissection functionality wherein said energy based dissection technology cannot operate, or operates differently, upon receipt of real time information from the nerve monitoring functionality that nerve damage may be imminent in the absence of such safety shutdown and removing human error and reaction time issues which prevents unintended dissection and concomitant nerve damage.

SUMMARY

The present invention provides a solution to the unmet need, by providing an apparatus comprising:

a. a connection to: (i) an energy source capable of powering the apparatus; (ii) an energy based dissection device; and (iii) a nerve integrity monitoring device; and
b. a communication link between:
   i. said energy based dissection device; and
   ii. said nerve integrity monitoring device wherein said nerve integrity monitoring device is capable of monitoring the integrity of a given nerve;
   iii. wherein said communication link is capable of receiving information supplied by said nerve integrity monitoring device and transmitting information to the energy based dissection device; performing the steps of:
      1. receiving information from said nerve integrity monitoring device;
      2. interpreting said information;
      3. upon determining a nerve integrity reading that indicates that nerve integrity will likely be compromised by continued operation of the energy based dissection device;
      4. transmitting a functional control command to said energy based dissection device.

There are many alternative embodiments to the device of the present invention described elsewhere herein.

It will be appreciated by one of skill in the art the many applications of the device of the present invention and should not be limited by the examples presented herein. For example, and not by way of limitation, any type of energy utilized in dissection may be suitable for use with the device of the present invention. Similarly, any type of nerve or other tissue capable of its integrity being monitored through basic electrode conduction may be suitable for use with the present invention.

BRIEF DESCRIPTION OF THE DRAWINGS

FIG. 1 shows one embodiment of the present invention. The central unit (1) receives an input of energy from an energy source (5) to power all functionality by powering on the central unit with switch (6). After powering on, the central unit (1) supplies power to the nerve monitoring device (3) and the energy based dissection device (2). The nerve monitoring device (3) is connected to the patient (not shown) according to its normal procedure and provides readouts (4) indicating nerve integrity. The central unit (1) also receives information regarding nerve integrity and may adjust or shut off power to the energy based dissection device (2) according to its programming. The central unit (1) may also provide an override switch (7) in order that a surgeon has ultimate decision authority as to energy flow to the energy based dissection device (2).

FIG. 6 shows an alternative embodiment of the device of the present invention wherein external beacons (12) are placed in proximity to the nerve to be monitored (11)

wherein said beacons (12) are capable of monitoring emissions of energy pulses (22) from the energy based dissection device (2) and reflections thereof.

DETAILED DESCRIPTION

For clarity of disclosure, and not by way of limitation, the detailed description of the invention is divided into the following subsections that describe or illustrate certain features, embodiments or applications of the present invention.

Definitions

An "energy based dissection device" as used herein refers to any device capable of converting an energy supply into a tool useful for creating a surgical incision or any type of tissue division or separation.

An "energy supply" is any form of energy, capable of, and suitable for, delivering a surgical incision.

A "nerve integrity monitoring device" as used herein refers to any device capable of monitoring nerve integrity.

"Nerve integrity" as used herein refers to maintaining the normal functioning of, within accepted medical tolerance limits, nerve impulse transmission pathways.

A "beacon" is an appropriate energy pulse generator and/or receptor capable of, in certain embodiments, either or both generating and receiving energy pulses. In certain embodiments, they may also be capable of receiving reflections of energy pulses and/or monitoring characteristics of said pulses.

The System of the Present Invention

In one embodiment the present invention provides an apparatus comprising:
  a. a connection to: (i) an energy source capable of powering the apparatus; (ii) an energy based dissection device; and (iii) a nerve integrity monitoring device; and
  b. a communication link between:
    i. said energy based dissection device; and
    ii. said nerve integrity monitoring device wherein said nerve integrity monitoring device is capable of monitoring the integrity of a given nerve;
    iii. wherein said communication link is capable of receiving information supplied by said nerve integrity monitoring device and transmitting information to the energy based dissection device; performing the steps of:
      1. receiving information from said nerve integrity monitoring device;
      2. interpreting said information;
      3. upon determining a nerve integrity reading that indicates that nerve integrity will likely be compromised by continued operation of the energy based dissection device;
      4. transmitting a functional control command to said energy based dissection device.

In one embodiment, the present invention would not be merely a connecting apparatus but would incorporate some or all components into one unified device.

In one embodiment, the nerve integrity monitoring device would be combined with the energy based dissection device such that the nerve integrity monitoring device sensors would be encased within, and at or near the cutting member of, the energy based dissection device.

In one embodiment, the functional control command that would be sent to the energy based dissection device in response to obtaining a nerve integrity reading that nerve integrity is likely to be compromised by continued operation of the energy based dissection device is a shutoff command.

In one embodiment, a shutoff command would have a manual user override.

In one embodiment, a manual user override would be housed on the apparatus. In another embodiment, a manual user override would be housed directly on the energy based dissection device and/or in close proximity to all other normally utilized surgical controls of the energy based dissection device.

In one embodiment, a shutoff command would be of a predetermined length of time. Such length of time would be operator-adjustable. Alternatively, once a shutoff command is transmitted, an affirmative signal to enable energy flow restoration to the energy based dissection device must be manually given by the user.

In one embodiment, the functional control command that would be sent to the energy based dissection device in response to obtaining a nerve integrity reading that nerve integrity is likely to be compromised by continued operation of the energy based dissection device is a reduction of energy to slow the dissection of the energy based dissection device.

In one embodiment, a reduction of energy command would have a manual user override.

In one embodiment, a manual user override would be housed on the apparatus. In another embodiment, a manual user override would be housed directly on the energy based dissection device and/or in close proximity to all other normally utilized surgical controls of the energy based dissection device.

In one embodiment, a reduction of energy command would be of a predetermined length of time. Such length of time would be operator adjustable. Alternatively, once a reduction of energy command is transmitted, an affirmative signal to enable full energy flow restoration to the energy based dissection device must be manually given by the user In one embodiment, the nerve integrity monitoring device would perform exactly as it does without the apparatus, i.e., sending normal visual and/or auditory and/or tactile signals to the user irrespective of signals that would be sent to the apparatus.

In one embodiment, the device of the present invention would have a baseline establishment function, wherein the operator could completely remove any operation of the energy based dissection device thereby establishing beyond doubt that there could be no effect of the energy based dissection device on nerve function or integrity and then pressing a reset button or other similar reset functionality to establish a new baseline readout from the nerve integrity monitoring device.

In one embodiment, the device of the present invention would have controls to adjust detection sensitivity threshold based on initial baseline parameters.

In one embodiment, the device of the present invention would provide a test pulse function, wherein the operator would be able to deliver a short duration lower energy burst from the energy based dissection device to an area where it may be thought to be at risk to test the area and review any change in readout from the nerve integrity monitor device prior to delivering a full energy cutting function. Such functionality could be implemented by including an energy dial to reduce the energy delivered to the energy based dissection device or a button that would automatically deliver a predetermined lower energy burst for a predetermined time period through the energy based dissection device before restoring the energy to normal power. The test pulse would be operator adjustable for energy strength and time of duration.

In one embodiment, the device of the present invention would have all functionality switches and buttons allowing operator chosen commands to be placed on the floor to be operated by foot allowing the operator full hand availability for operating procedures. Such foot controls could be hard wired or connected wirelessly to the device of the present invention.

Energy based dissection devices have become commonplace in the modern operating room as a result of their improved efficiencies and precision.

For example, Medtronic provides the PlasmaBlade™ which are a family of disposable cutting and coagulation devices that offer the exacting control of a scalpel and bleeding control of traditional electrosurgery without extensive collateral damage. The PlasmaBlade™ is based on pulsed plasma technology which represents an advancement of radiofrequency surgical technologies.

In another example, Covidien provides the Sonicision™, a cordless ultrasonic dissection device. Covidien advertises that its Sonicision™ device results in "faster dissection than the Harmonic™" device (referring to the Ethicon Harmonic Ace™ device referenced elsewhere herein).

In another example, Covidien provides a portfolio of energy based dissection devices under the ForceTriad™, Valleylab™ and LigaSure™ brands employing a variety of technology including monopolar and bipolar electrosurgery components.

Generally, electrosurgery refers to the cutting and coagulation of tissue using high-frequency electrical current. Electrical current is created by the movement of electrons and voltage is the force that creates this movement. There are two types of electrical current—direct current (DC), where the electrons always flow in the same direction, and alternating current (AC), where the current changes direction periodically. With AC, each time the current reverses, it is considered one cycle. Frequency refers to the number of cycles in one second and is measured in hertz (Hz).

Basic electrosurgery units used in operating rooms convert standard AC frequencies, i.e., 50 Hz to 60 Hz as delivered from a typical wall outlet to much higher frequencies such as from 500,000 Hz to 3,000,000 Hz. This is necessary to minimize nerve and muscle stimulation, which occurs at frequencies below 10,000 Hz.

Basic electrosurgery units are subject to electromagnetic interference, either interruption of their normal operating parameters by other instruments generating a nearby electrical field or interfering with the normal operation of other nearby instruments.

Certain non-electrical energy based dissection devices may overcome this interference. Examples include, but are not limited to, ultrasonic energy based dissection devices and thermal energy based dissection devices.

All of these devices have some type of thermal and/or electrical spread, i.e., the surgeon intends to cut through a specific tissue and at least a minimal amount of adjacent tissue is affected. The key is to minimize the spread so that a minimal amount of adjacent tissue is affected with unintended consequence. Of significant importance is when such adjacent tissue is nerve tissue.

Another consideration is interference with intra-operative monitoring equipment. Responses have included functionality that includes argon beam coagulation, lasers, ultrasound, saline enhancement and ferromagnetic technology for minimizing the need for actual electric current passing through tissue.

Nerve integrity monitoring devices have also become commonplace in the modern operating room where certain surgeries place at risk damage to significant nerve tissues.

For example, Medtronic's NIM-Neuro® 3.0 nerve integrity monitoring system provides an eight-channel nerve monitoring system delivering advanced monitoring features such as simultaneous monitoring during bipolar cautery, real-time continuous monitoring with an APS™ electrode, artifact detection software to help reduce noise, signal overlay in a microscope, use of two stimulators at one time, touchscreen operation, and audio and visual alerts.

In another example, Natus® Neurology provides the XLTEK Protektor 32™ IOM system with multimodality monitoring, configurable stimulus interleaving, nerve integrity monitoring mode to identify neural structures and confirm efferent nerve function and selectable stimulator contact chimes.

In another example, NuVasive™ provides its NVM5® nerve monitoring system for real-time, precise and reliable feedback to ensure nerve and spinal cord safety. By using this unique and advanced technology, the surgeon is provided with intraoperative information about the location and function of the nerves.

In all of the foregoing examples, the surgeon is provided information, either in the form of an audible or visual signal or some type of wave readout that must be first received and then understood prior to the surgeon reacting. Thus, there is room for surgeon error in interpretation as well as reaction time issues in utilizing the existing nerve monitoring technology.

In one embodiment, the device of the instant invention provides an apparatus wherein any one of the foregoing examples of energy based dissection devices or some other equally suitable energy based dissection device is connected to the apparatus such that the apparatus delivers, with the capability to control, the flow of energy to the energy based dissection device. Alternatively, the energy based dissection device may be powered separately and the apparatus is merely capable of interrupting and/or altering the flow of energy to the energy based dissection device.

In one embodiment, the device of the instant invention provides an apparatus wherein any one of the foregoing examples of nerve integrity monitoring devices or some other equally suitable nerve integrity monitoring device is connected to the apparatus such that the apparatus is capable of receiving information from the nerve integrity monitoring device. The apparatus may power the nerve integrity monitoring device or the nerve integrity monitoring device may be powered separately.

In one embodiment, the device of the instant invention provides an apparatus which, upon receiving information from the nerve integrity monitoring device, is capable of interpreting the information received to determine if nerve integrity is likely to be compromised by continued exposure to levels of energy that triggered the reading in the first instance.

In one embodiment, the device of the instant invention provides an apparatus that upon interpreting information that nerve integrity is likely to be compromised, is capable of delivering an appropriate command to the energy based dissection device. An appropriate command may be one that simply shuts off energy to the energy based dissection device. Another appropriate command may be one that reduces the flow of energy to the energy based dissection device.

Nerve integrity monitoring devices typically provide functionality by providing electrodes that are in functional contact with a nerve to be monitored. The nerve integrity monitoring devices can then detect whether the nerve at issue is functioning normally and providing an unbroken circuit or if the nerve has been damaged and cannot complete the circuit normally.

Figure 1:
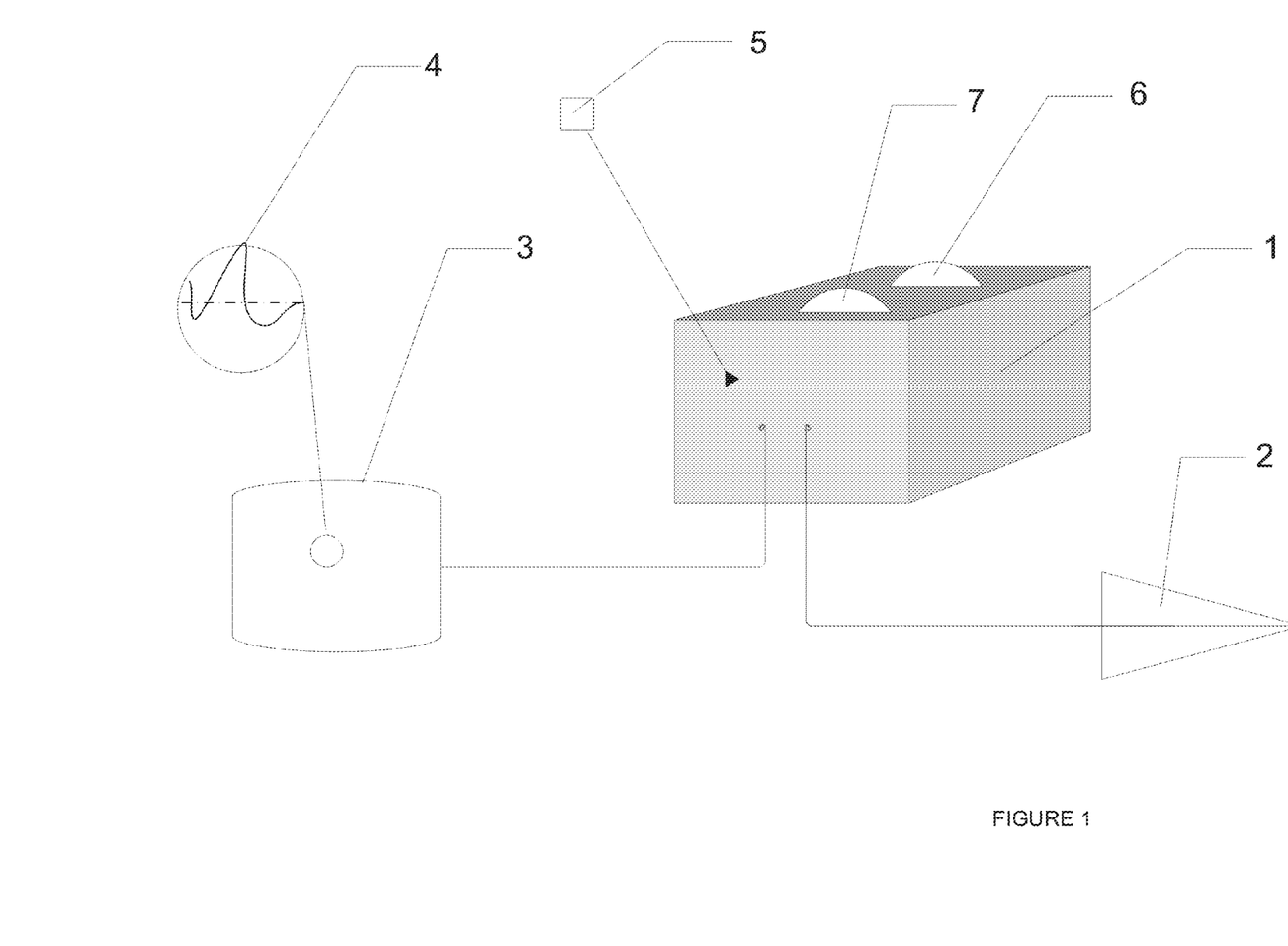
Figure 2:
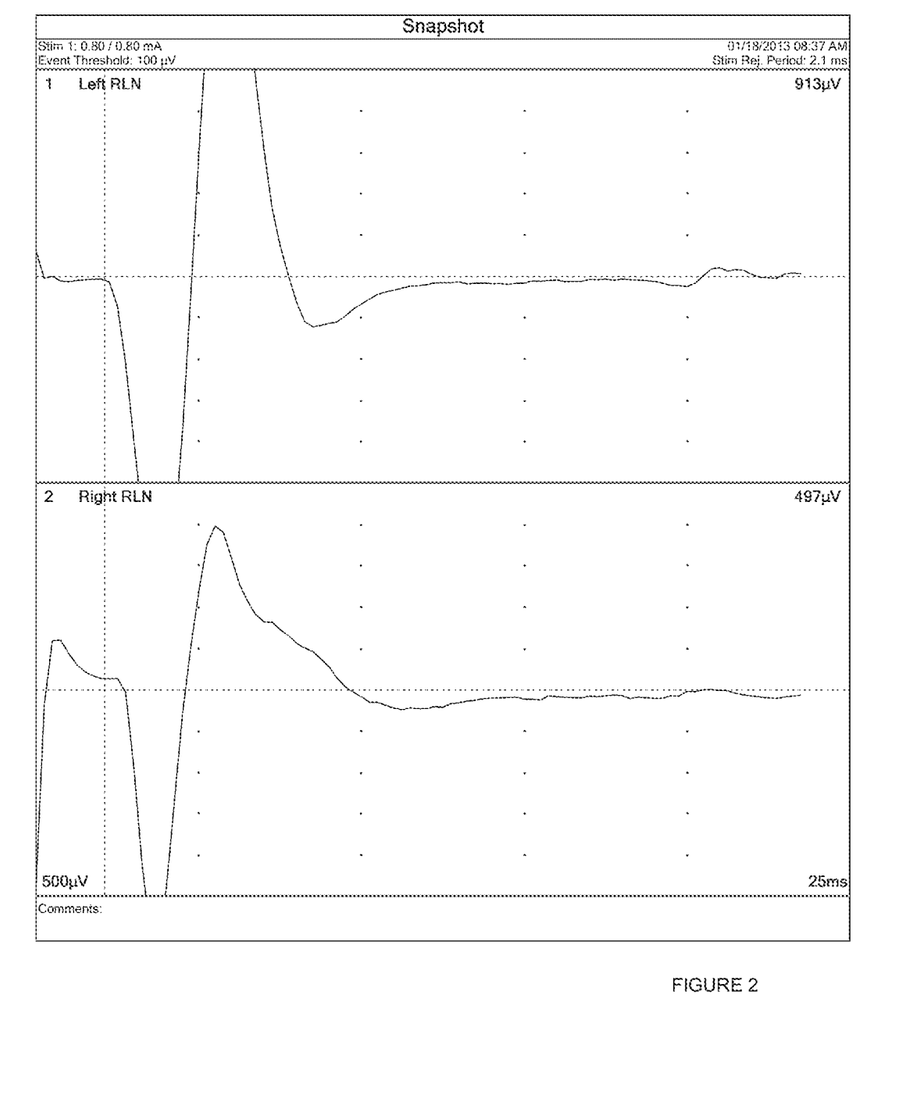
FIG. 2 shows one potential readout of a nerve monitoring device in response to monitoring of a laryngeal nerve during surgery.

In FIG. 2, the wave readouts demonstrate that the nerve at issue (in this case a recurrent laryngeal nerve ("RLN") which is at risk in thyroid, parathyroid and other surgeries performed close to the course of the RLN) is functioning as expected when an external stimulus is present.

Figure 3:
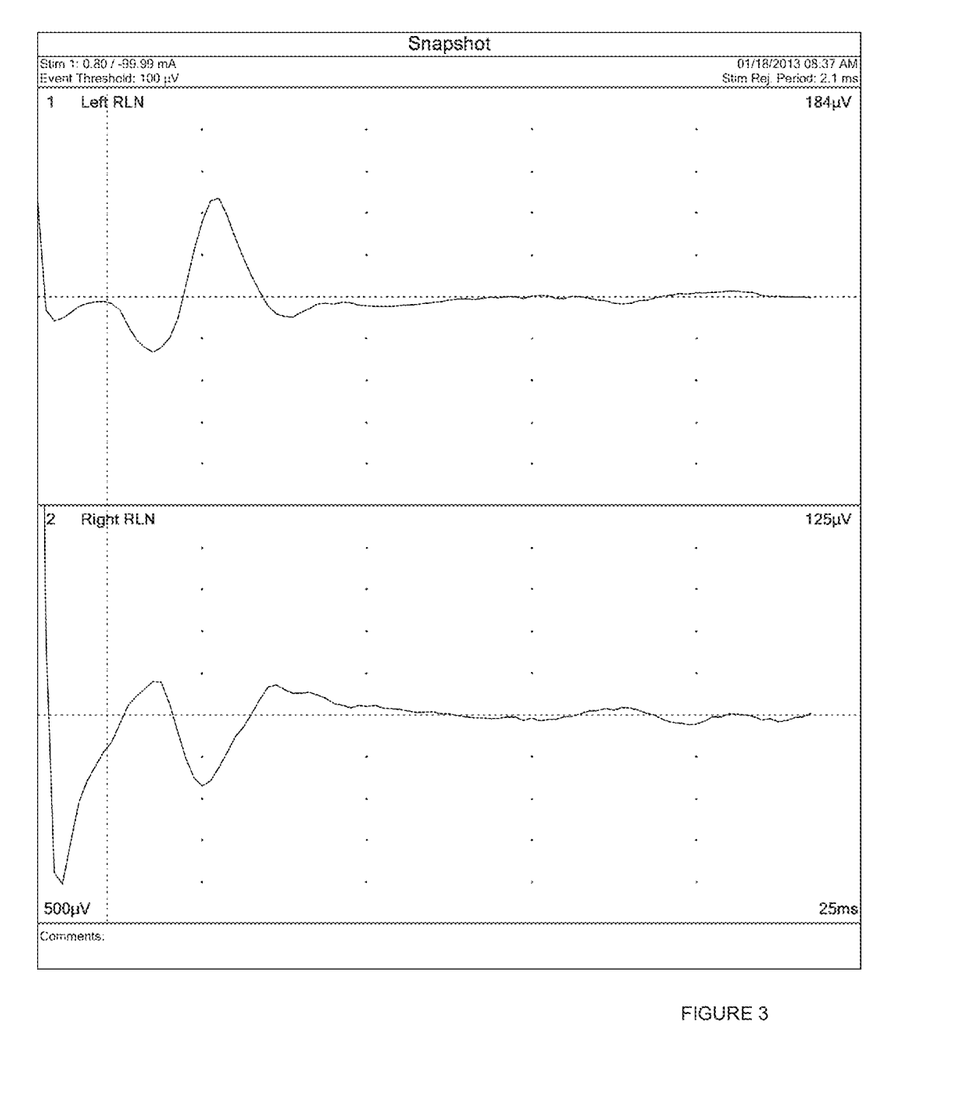
FIG. 3 shows another potential readout of a nerve monitoring device in response to monitoring of a laryngeal nerve during surgery.

In FIG. 3, the wave readouts (again, in the case of an RLN) similarly demonstrate expected functionality. The differences between FIGS. 2 and 3 reflect the differences in stimuli, the actual proximity to the RLN (i.e, direct contact versus immediate proximity), the specific location along the RLN that the stimulus occurs, and the like.

Figure 4:
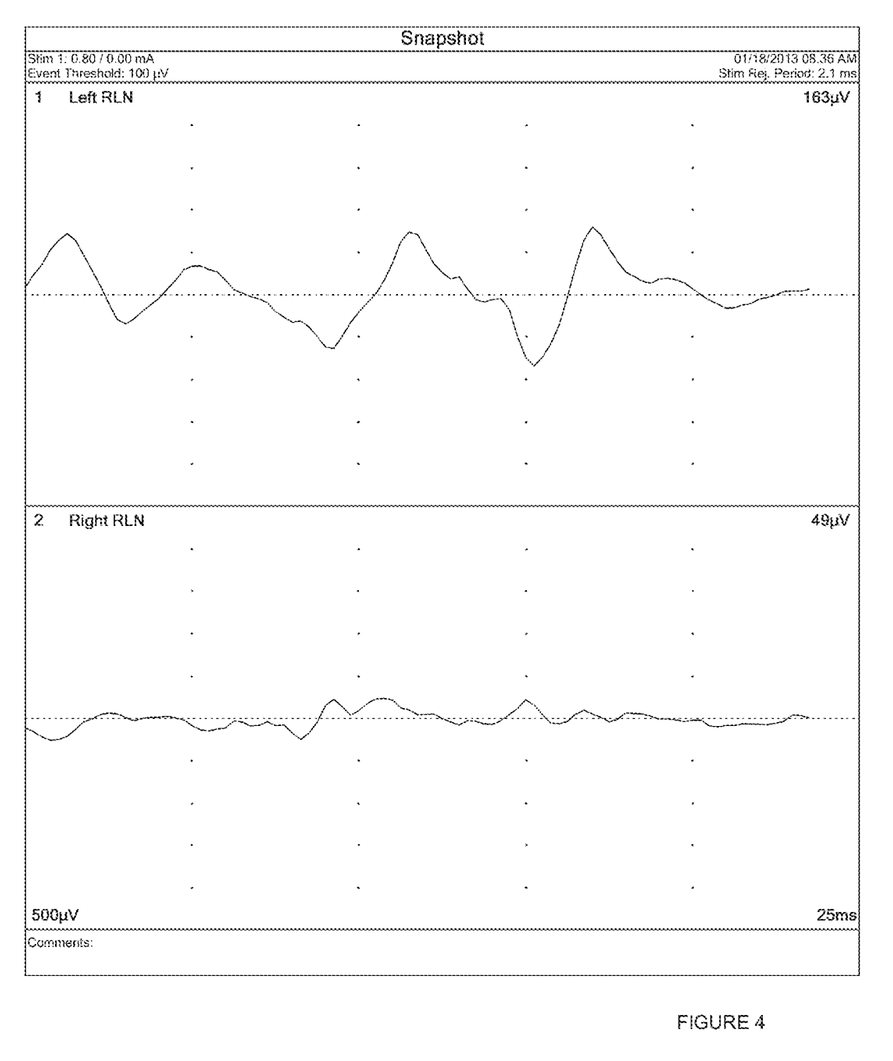
FIG. 4 shows another potential readout of a nerve monitoring device in response to monitoring of a laryngeal nerve during surgery.

In FIG. 4, the wave readouts (again, in the case of an RLN) demonstrate an RLN that is experiencing nearby or indirect stimulus (traction and/or physical trauma).

Figure 5:
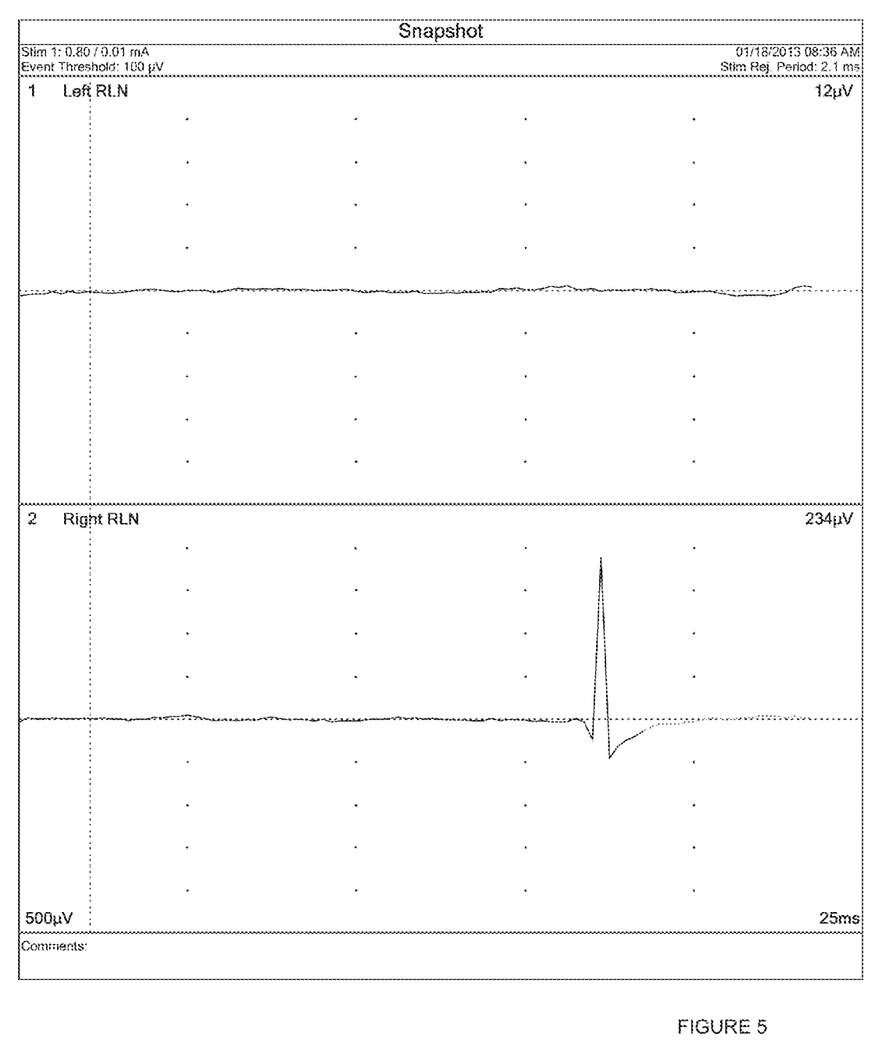
FIG. 5 shows another potential readout of a nerve monitoring device in response to monitoring of a laryngeal nerve during surgery.
Figure 6:
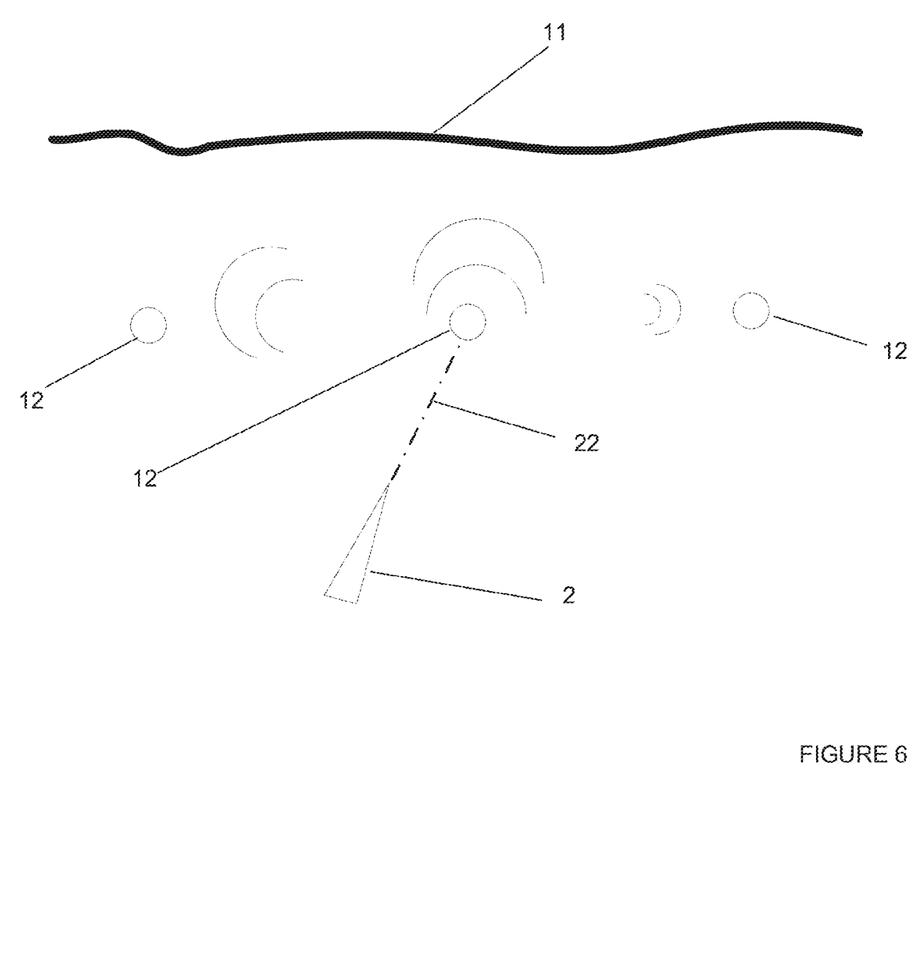

In FIG. 5, (again, in the case of an RLN), the top wave readout indicates an RLN that is undisturbed, while the bottom wave readout indicates an RLN that is undisturbed for a period of time and then indicates a stimulus of expected RLN functionality.

Reference to the foregoing figures demonstrate that a variety of wave readouts are possible based upon many factors such as the actual nerve to be monitored, the strength of the energy wave of the energy based dissection device, the method of monitoring nerve integrity and actual proximity to the nerve of the energy based dissection device when an energy pulse is delivered.

One of skill in the art will appreciate that where all other variables are constant and/or predetermined and accurately measured and controlled, the actual and/or relative proximity to the nerve to be monitored may be determined by interpreting the nerve monitoring device wave readouts.

This nerve proximity monitoring function can be implemented to create a nerve mapping function based on interpreting data gathered simultaneously from multiple electrodes at various points along a particular nerve, and/or from mathematical vector analysis of the nerve monitoring waveform resulting from single or multiple energy stimuli.

Each time a nerve senses an electrical impulse, it reacts in a way that provides a specific wave readout in the nerve monitoring device. As noted, these wave readouts can be interpreted to provide a shutoff command to the energy based dissection device when such device is so close to the nerve to be monitored that continued supply of energy is likely to damage the nerve integrity. Such readouts can also be used to determine nerve proximity and nerve mapping. By continuously determining such nerve proximity, changes in proximity can be measured and create a vector mapping of nerve location and orientation. By sensing against predetermined areas along a nerve, three dimensional nerve mapping can be accomplished. By plotting this information against known nerve structure, an accurate indication can be determined of likely nerve location, size and orientation in relation to the current location of the energy based dissection device. The more readings that are obtained, the more accurate this nerve location plotting can be.

Inherent in the waveform readouts from a nerve integrity monitoring device are vector data. A vector is a quantity that has both direction and magnitude. Nerves function by conducting energy along its length, i.e., the nerve integrity is measured by the magnitude and direction of such energy conduit. A given nerve is generally known in terms of its size, shape, ability to conduct energy and relative location within any particular patient based on that patient's age, size, condition and other criteria. Based on a library of a multitude of prior readings from subjects similar to a given patient and a baseline reading from the specific patient, mathematical vector analysis on the vector data contained within given waveform readouts can be used to project an accurate real-time mapping of the given nerve relative to the location of the energy based dissection device. As the operator moves the energy based dissection device, the relative distance from it to a given point along the given nerve changes. This new data, also containing vector data, is used to continuously update and refine the relative location of the given nerve to the energy based dissection device. For example, a given nerve of a given size and condition will be expected to generate a waveform of certain characteristics within tolerance limits in response to stimuli of a given energy pulse at a certain distance. Moreover, that nerve will be known to exist generally in size and location within a patient and to conduct energy in a certain direction. The operator can establish a baseline by providing a known energy pulse at a known distance to a specific nerve in an area where such movements and locations can be readily observed. Once these initial readings are established and comport with expected values, then, as the operator moves into the surgery, all waveforms will be analyzed against these known parameters. One of ordinary skill in the art will appreciate that using vector data analysis, an accurate plot of the actual nerve size and location relative to the energy based dissection device can be performed.

In one embodiment, the nerve integrity can be monitored along multiple points of its trajectory, and/or through vector analysis of the waveform. Thus, when the energy based dissection device sends out an energy pulse, multiple wave readouts ensue simultaneously, each bearing specific characteristics, including vector data, based upon the proximity of that particular sensor point to the energy based dissection device. Thus, the plotting of the nerve location and orientation with respect to the energy based dissection device can be even more accurate.

In one embodiment, this nerve location and orientation is plotted in real time on a graphical display on the device of the present invention.

In one embodiment, nerve location and orientation information can be supplemented with information beacons. In one embodiment, beacons capable of delivering energy pulses can be placed in situ into nearby soft tissue and held in place with prongs prior to beginning a surgical procedure. The beacons could be wireless or connected to either the energy based dissection device or the nerve integrity monitoring device or a separate communicatively connected functional apparatus within the device of the present invention with wires. Such beacons would emit a known energy pulse at various known frequencies and duration to be received by the electrodes monitoring nerve integrity. In this manner, the nerve size, location, orientation and integrity can be monitored relative to the beacon pulses prior to any energy pulse generated by the energy based dissection device in all of the same ways as just discussed. Then, when the energy based dissection device is introduced into the equation, the known energy being introduced by said device is compared to the readings obtained by the beacon pulses. In this manner, information will be generated to determine the proximity of the beacons to the nerve and with greater accuracy, the proximity of the energy device to the beacons and thus, the nerve.

In one embodiment, the beacons could also receive energy signals and detect the nerve data independent of and in addition to the nerve integrity monitoring device, and also detect the energy based dissection device. The nerve integrity monitoring device is still needed to monitor actual nerve integrity. However, the additional information gathered from reflected energy pulses between the beacons and the nerve and the energy based dissection device and the beacons will yield greater accuracy of nerve location, size, and orientation.

EXAMPLES

For clarity of disclosure, the following examples are based on a typical thyroid surgery procedure that potentially harms the RLN. One of ordinary skill in the art will appreciate the many embodiments of the system of the present invention, for example, and not by way of limitation, back or spinal surgery, surgery proximate to the optic nerve, surgery proximate to the brain stem, and the like.

In a typical thyroid surgery, RLN injury is a dreaded potential complication because surgical cutting devices usually operate in close proximity to the RLN during surgery. With the advance of surgical cutting devices, including the use of energy based dissection devices, the cutting (and other unwanted trauma) can happen in an instant.

Mechanisms of RLN injury may include transection, stretch/traction, crush, ligature entrapment, electrical, thermal, and ischemia.

Factors that increase risk of RLN injury may include re-operation to correct an issue, non-identification of the RLN, inexperience, variances in anatomy, or other unexpected variables such as goiter size and location.

Any device that can minimize these risk factors is desirable.

The early devices and methods aimed at reducing risk include devices to identify and monitor RLN integrity.

For example, use of hook-wire electrodes placed endoscopically into the thyroarytenoid muscles to track ongoing EMG over continuously updated sampling epochs.

In another example, subdermal electrodes are endoscopically placed bilaterally into the posterior cricoarytenoid muscles.

However, there are disadvantages of intramuscular EMG electrode placement such as, such placement is "blind" and subject to dislodgment.

Surface electrodes have been implemented. An example is an electrode consisting of paired silver flexograph plates attached to a polyethylene base, which is curved to conform to the postcricoid area.

Advances now include the use of an EMG endotracheal tube consisting of a low-pressure cuffed silicone elastomer tube with integrated bilateral paired 0.16 inch diameter stainless steel wire electrodes that run in protective channels along the tube and are exposed for 30 millimeters at the glottis lovel and skewed anterolaterally for vocal cord contact and provides for continuous tracking of EMG activity.

Once anesthesia is induced, the endotracheal tube is placed such that the vocal cord is in true contact with the exposed electrodes. Baseline stimulation is recorded to insure identification of the RLN and recognition of an event that causes such stimulation. The surgery is then conducted.

After the surgical specimen is removed, the RLN is again stimulated to insure post procedure integrity.

If, during the surgery, the surgeon recognizes a stimulus pattern (such as those indicated in FIGS. 2-4) wave readout from the nerve integrity monitoring device, he knows that he is stimulating the RLN and needs to cease doing whatever it is that he was doing at that moment and re-establish a safe operating pathway.

Other surgical advances include the use of energy based dissection devices, such as those described above. They provide for near instantaneous dissection along a surgical path. The danger is that if that surgical path erroneously is an unsafe operating pathway, damage can be done to the RLN prior to the ability of the surgeon to recognize a stimulus pattern (such as those indicated in FIGS. 2-4) that indicates inadvertent stimulus resulting in damage to the RLN.

The device of the present invention provides a way to eliminate surgeon reaction time and surgeon error in recognition by providing a device that receives the wave readout information in real time and simultaneously interprets such wave readouts and upon interpreting a readout that indicates any potential damage to the RLN, cuts power to the energy based dissection device such that even if the surgeon does not have time to react, the RLN will cease being stimulated.

This will give time to the surgeon to consider his pathway, identify potential damage, and restart the procedure prior to any damage to the RLN occurring.

One of skill in the art will appreciate the type of interpretative analysis needed in connection with any specific wave readout or other form of signal generated by nerve integrity monitoring devices and what immediate response is necessary to protect RLN (or other nerve, in the case of other types of surgeries to which this device is applicable) functionality.

One of skill in the art will also appreciate if full shutoff of energy to the energy based dissection device is required or if allowable to proceed at reduced on a minimal stimulus reading. Similarly, it may be desirable to have a manual override to continue with a procedure despite the risk disclosed. Surgeon expertise is not impacted, but rather enhanced by providing potential error correction and reaction time assistance.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

Each and every feature described herein, and each and every combination of two or more of such features, is included within the scope of the present invention provided that the features included in such a combination are not mutually exclusive.

What is claimed is:

1. A surgical apparatus comprising:
   an energy based dissection device;
   a power source for said energy based dissection device;
   a nerve integrity monitoring device adapted to detect first energy signals associated with a selected nerve;
   a plurality of each of said plurality of beacons configured to emit a respective energy pulse having a predetermined frequency, a predetermined duration, and a predetermined energy level, and to receive second energy signals associated with the selected nerve; and a processing device configured to receive first information relating to the first energy signals, from the nerve integrity monitoring device, and second information relating to the second energy signals, from the plurality of beacons, interpret said first information and said second information, determine whether or not an integrity of selected nerve is likely to be compromised based on the first information and second information, and cause a shutoff command to be automatically transmitted to the energy based dissection device, when it is determined that the integrity of selected nerve is likely to be compromised.

2. The apparatus of claim 1 wherein each of said plurality of beacons is further configured to detect signals associated with energy pulses emitted by other beacons among the plurality of beacons.

3. The apparatus of claim 1 wherein each of said plurality of beacons is further configured to detect additional electrical signals emitted by said energy based dissection device.

4. The apparatus of claim 3 wherein the processing device further comprises software configured to utilize data received from said plurality of beacons to determine a location of the energy based dissection device relative to each of said plurality of beacons.

5. The apparatus of claim 1 wherein the processing device further comprises software configured to utilize data from the nerve integrity monitoring device to determine a location of the energy based dissection device.

6. The apparatus of claim 5 wherein said software is further configured to utilize data from said plurality of beacons to determine the location of the energy based dissection device.

7. The apparatus of claim 1 wherein the processing device further comprises software configured to utilize data received from said plurality of beacons to map a location of nerve tissue.

8. The apparatus of claim 1 wherein the processing device further comprises software configured to utilize data received from said plurality of beacons and the nerve integrity monitoring device to map location of nerve tissue.

9. The apparatus of claim 1 wherein the processing device further comprises software configured to utilize data received from said plurality of beacons and predetermined information included in the software of the nerve integrity monitoring device to map a real-time location of the energy based dissection device relative to nerve tissue.

10. The apparatus of claim 1 wherein each of said plurality of beacons communicates wirelessly with one of the energy based dissection device and the nerve integrity monitoring device.

11. The apparatus of claim 1 wherein each of said plurality of beacons is connected via one or more wires to one of the energy based dissection device and the nerve integrity monitoring device.

12. The apparatus of claim 9 wherein the nerve integrity monitoring device is further adapted to generate first vector data and each of said plurality of beacons is further adapted to generate second vector data.

13. The apparatus of claim 12 wherein the software interprets the information supplied by the nerve integrity monitoring device and each of said plurality of beacons through the use of vector analysis.

14. The apparatus of claim 1 wherein said energy based dissection device is configured to emit an energy burst for a predetermined time, at a predetermined frequency and at a predetermined power level, said energy burst sufficient in frequency and power level to be detected by one or more of the plurality of beacons but insufficient in frequency and power level to damage tissue.

15. The apparatus of claim 1 further comprising a manual override to the shutoff command.

16. The apparatus of claim 1 wherein a precise location of each of said plurality of beacons is known by the apparatus.

17. The apparatus of claim 1 wherein a determination that the information indicates that an integrity of the selected nerve is likely to be compromised is made based on one of the following: an EMG response measured by the nerve integrity monitoring device; radio frequency signals detected by one or more of the plurality of beacons; energy levels detected by one or more of the plurality of beacons; the location of the energy based dissection device relative to a digitally mapped nerve location; the location of the energy based dissection device relative to one or more of the plurality of beacons.

18. A surgical apparatus comprising:
an energy based dissection device;
a power source for said energy based dissection device;
a nerve integrity monitoring device adapted to detect first energy signals associated with a selected nerve tissue;
a plurality of beacons, each of said plurality of beacons configured to emit a respective energy pulse having a predetermined frequency, a predetermined duration, and a predetermined energy level, and to receive second energy signals associated with the selected nerve tissue; and
a processing device further comprising software configured to perform the following steps:
receive first information relating to the first energy signals from the nerve integrity monitoring device and second information relating to the second energy signals from the plurality of beacons;
determine a location of the selected nerve tissue based on the first information and the second information;
determine a location of the energy based dissection device based on the first information and second information;
determine a spatial relationship between the location of the selected nerve tissue and the location of the energy based dissection device;
determine whether the spatial relationship between the location of the energy based dissection device and the location of the selected nerve tissue satisfies one or more predetermined criteria; and
cause a shutoff command to be automatically transmitted to the energy based dissection device, if the spatial relationship between the location of the energy based dissection device and the location of the selected nerve tissue satisfies the one or more predetermined criteria.

* * * * *